United States Patent
Restorp et al.

(10) Patent No.: US 9,551,111 B2
(45) Date of Patent: Jan. 24, 2017

(54) CHEMICAL COMPOUNDS

(71) Applicant: AKZO NOBEL CHEMICALS INTERNATIONAL B.V., Amersfoort (NL)

(72) Inventors: Per Anders Restorp, Göteborg (SE); Arne Olov Roland Andersson, Stenungsund (SE); Nils Erik Ronne, Uppsala (SE)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 86 days.

(21) Appl. No.: 14/367,263

(22) PCT Filed: Dec. 20, 2012

(86) PCT No.: PCT/EP2012/076254
§ 371 (c)(1),
(2) Date: Jun. 20, 2014

(87) PCT Pub. No.: WO2013/092778
PCT Pub. Date: Jun. 27, 2013

(65) Prior Publication Data
US 2015/0059997 A1 Mar. 5, 2015

Related U.S. Application Data

(60) Provisional application No. 61/580,356, filed on Dec. 27, 2011.

(30) Foreign Application Priority Data

Dec. 23, 2011 (EP) .................................... 11195501

(51) Int. Cl.
*D21H 21/16* (2006.01)
*D21H 17/07* (2006.01)
*C07D 205/04* (2006.01)

(52) U.S. Cl.
CPC ............ *D21H 21/16* (2013.01); *C07D 205/04* (2013.01); *D21H 17/07* (2013.01)

(58) Field of Classification Search
USPC ...... 162/158, 183–185; 106/2; 548/100, 952
See application file for complete search history.

(56) References Cited

U.S. PATENT DOCUMENTS

| 3,066,032 | A | * | 11/1962 | Fukushima | ................ C08L 1/24 |
| | | | | | 106/162.6 |
| 3,144,417 | A | * | 8/1964 | Bailey, Jr. | ............... C08G 65/06 |
| | | | | | 508/225 |
| 5,176,891 | A | | 1/1993 | Rushmere | |
| 5,501,711 | A | | 3/1996 | Weltrowski et al. | |

FOREIGN PATENT DOCUMENTS

| DE | 1015574 | 2/1955 |
| GB | 1008464 | 10/1965 |
| GB | 1136842 | 12/1968 |
| WO | 03/087471 A1 | 10/2003 |
| WO | 2010/000696 A1 | 1/2010 |

OTHER PUBLICATIONS

Search Report of EP Application No. 11195501.9, dated Oct. 31, 2012.
International Search Report and Written Opinion of Application No. PCT/EP2012/076254, mailed Sep. 23, 2013.
Jarry et al, "Synthesis and Pharmacological Properties of Some 5-dialkylaminomethyl 2-amino-2-oxazolines," European Journal of Medicinal Chemistry, Editions Scientifique Elsevier, Paris, FR, vol. 21, Jan. 1, 1986, pp. 138-142.
Burness, D.M., "Synthesis and Reactions of Quarternary Salts of Glycidyl Amines," Journal of Organic Chemistry, vol. 28, Sep. 1, 1963, pp. 2283-2288.
M. Ye-Hong et al, "Synthesis and Application of Fatty Amide Sizing Agent," Jiangsu Provincial Key Laboratory of Pulp and Paper Science and Technology, Nanjing Forestry University, Nanjing 210037, China, vol. 22, Sep. 2010, pp. 36-41—Abstract on first page.
Zhang et al, "Synthesis of 3[Methyl-1-naphthalenylmethyl]amino]-1,2-epoxypropane," Chinese Journal of Pharmaceuticals, 2006, vol. 37, pp. 82-83.
Kutkevicius, "Products of the Reaction of Epichlorohydrin with Aromatic Amines, SVIII, N-phenyl-I-naphthylamine," Chimia Geterosciekliceskih Soedinenij, No. 5, Jan. 1, 1974, pp. 685-688 (cited in EP Search Report).

(Continued)

*Primary Examiner* — Dennis Cordray
(74) *Attorney, Agent, or Firm* — McDonnell Boehnen Hulbert & Berghoff LLP

(57) ABSTRACT

Compounds according to formula (I)

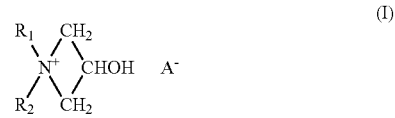

or formula (II)

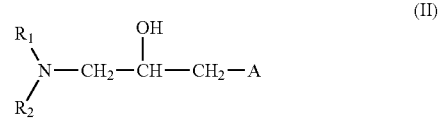

wherein $R_1$ and $R_2$, independently from each other, are chosen among hydrocarbons having from 1 carbon atom up to 30 carbon atoms, with the proviso that at least one of $R_1$ and $R_2$ are chosen among hydrocarbons having at least 8 carbon atoms, and A is a halogen. Use of compounds as hydrophobing agent, such as sizing agent.

9 Claims, No Drawings

(56) References Cited

OTHER PUBLICATIONS

George W. Sears, Jr., "Determination of Specific Surface Area of Colloidal Silica by Titration with Sodium Hydroxide," Grasselli Chemicals Department, Experimental Station, E.I. du Pont de Nemours & Co.,Inc., Wilmington, Del., vol. 28, No. 12, Dec. 1956, pp. 1981-1983.
R.K. Iler et al, "Degree of Hydration of Particles of Colloidal Silica in Aqueous Solution," Grasselli Chemicals Department, Experimental Station, E.I. du Pont de Nemours & Co.,Inc., Wilmington, Del., pp. 955-956.
V.R. Gaertner, "Ring-Opening Alkylations of 1,1-Dialkyl-3-Substituted Azetidinium Cations, Substituent Entropy-Controlled Strained Ring-Chain Equilibria," The Journal of Organic Chemistry, vol. 33, No. 2, Feb. 1968, pp. 523-530.
Ross, et al, "Some Reactions of Epichlorohydrin with Amines," Journal of Organic Chemistry, 29: (1964), pp. 824-826.
Vorozhtsov, N.N., Products of Epichlorophydrin with Aromatic Amines. I.gamma.-Cloro-beta-hydroxypropyl Derivatives of Amines and Products of Their Transformation, Zhurnal Obshchei Khimii, Jan. 1, 1957, pp. 2152-2160 (cited in EP Search Report).
Rothstein, "Reaction of Secondary Amines on the Epichlorohydrin Action," 1953, pp. 1050-1052—Machine Translation attached.
3 Intermediate Structures from ChemSpider, RSC Free Chemical Database, Sep. 28, 2011, pp. 1-3.

\* cited by examiner

CHEMICAL COMPOUNDS

This application is a national stage filing under 35 U.S.C. §371 of PCT/EP2012/076254, filed Dec. 20, 2012, which claims priority to European Patent Application No. 11195501.9, filed Dec. 23, 2011, and U.S. Provisional Patent Application No. 61/580,356, filed on Dec. 27, 2011, the contents of which are incorporated herein by reference in their entirety.

The present invention relates to novel nitrogen containing compounds and their preparation, the use of nitrogen containing compounds as hydrophobicity providing compounds, compositions comprising nitrogen containing compounds, a method for producing compositions, a process for the manufacturing of paper and board, and paper and board obtainable thereby.

The hydrophobicity of various substances may be increased by treatment with compounds having hydrophobic moieties. This utilised is in, for example, the field of paper and paper board that often need to have a certain degree of resistance to penetration of liquid and moisture. One way of providing paper and paper board having increased resistance to the penetration of liquid and moisture is to apply certain compounds in the paper making process. Such compounds, often referred to as sizing agents, may be added to the cellulosic suspension prior to the formation of a web of paper or paper board and/or to the formed web. The addition of sizing agents to the cellulosic suspension and prior to sheet formation is usually referred to as internal sizing or stock sizing, whereas the addition of sizing agents to the paper or paper board web is commonly referred to as surface sizing. Sizing agents usually comprise a hydrophobic functionality and may also contain moieties which can be chemically bonded to constituents in a cellulosic suspension or constituents in a web of cellulosic fibres, typically bonded to the cellulose fibres. Sizing agents which do not have the ability to react chemically are typically referred to as non-reactive sizing agents. Sizing agents which may chemically react with constituents in a cellulosic suspension, or constituents in a web of paper or paper board are often referred to as chemically reactive sizing agents, or cellulose-reactive sizing agents. Commonly applied cellulose-reactive sizing agents include ketene dimers, ketene multimers, acid anhydrides, organic isocyanates and carbamoyl chlorides. Sizing agents are usually not applied as such but are provided as aqueous compositions, in the form of emulsions or dispersions, mostly due to the hydrophobic character of the sizing agent. In order to properly disperse or emulsify a sizing agent additional compounds are usually used.

The Chinese paper "Synthesis and application of fatty amide sizing agent", M Ye-Hong et. al., Zaozhi Huaxuepin (2010), 22 (Suppl.), Nanjing Forestry University, pp 36-41, discloses cationic fatty amide sizing agents prepared by reacting stearic acid and diethylene triamine (DETA) thereby forming a stearic acid containing adduct and reacting said adduct with epichlorohydrin (EPI) to from a cationic fatty amide compound.

DE 1015574 discloses quaternary ammonium compounds derived from the reaction of secondary amines and halogen substituted epoxides. The hydrocarbon residues attached to the quaternary ammonium contain at the most seven carbon atoms.

The paper "Ring opening alkylations of 1,1-dialkyl-3-substituted azetidinium cations: substituent entropy controlled strained ring-chain equilibrium with amined", Gaertner, Journal of Organic Chemistry, 33: 523-530 (1968) discloses 1,1-dialkyl-3-hydroxyazetidinium cations for alkylation of a variety of active nucleophiles.

The document "Some reactions of epichlorohydrine with amines" Ross et. al., Journal of Organic Chemistry, 29: 824-826 (1964) relates to a study of the reaction of epichlorohydrin with ethylene diamine.

An object with the present invention is to provide an alternative hydrophobing agent of high efficiency, such as a sizing agent for paper making.

A further object of the invention is to provide a hydrophobing agent which can be easily emulsified/dispersed in water.

Still a further object of the invention is to provide an alternative hydrophobing agent which is easily prepared of readily available raw materials.

Still a further object of the invention is to provide a hydrophobing agent which exhibit good retention properties, for example when used as an internal sizing agent at paper making.

The above objects can be achieved by the provision of a compound according to formula (I)

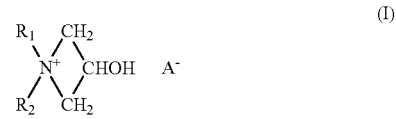

wherein $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 8 carbon atoms, and A is a halogen.

Another aspect of the invention concerns a compound of the formula (II)

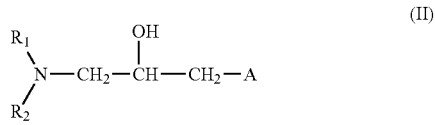

wherein $R_1$ and $R_2$, independently from each other, are chosen among hydrocarbons having from 1 carbon atom up to 30 carbon atoms, with the proviso that at least one of $R_1$ and $R_2$ are chosen among aliphatic hydrocarbons having at least 8 carbon atoms, and A is a halogen.

Another aspect of the invention concerns a method for producing a compound chosen among compounds of formula (I) as defined above, formula (II) as defined above, and mixtures thereof, the method comprising reacting compounds of formula (III) and formula (IV), compounds of formula (III) being represented by:

compounds of formula (IV) being represented by:

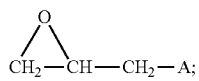

wherein $R_1$ and $R_2$ are as defined above and, where applicable, A is a halogen. Thus, for preparation of compounds of formula (I), $R_1$ and $R_2$ are, independently from each other, chosen among hydrocarbons having from 1 carbon atom up to 30 carbon atoms, with the proviso that at least one of $R_1$ and $R_2$ are chosen among preferably aliphatic hydrocarbons having at least 8 carbon atoms. For preparation of compounds of formula (II), at least one of $R_1$ and $R_2$ are chosen among aliphatic hydrocarbons having at least 8 carbon atoms.

A further aspect of the invention concerns use of a compound chosen among compounds of formula (I), formula (II), formula (V), and mixtures thereof, for providing hydrophobocity (i.e. as a hydrophobing agent) compounds of formula (V) being represented by:

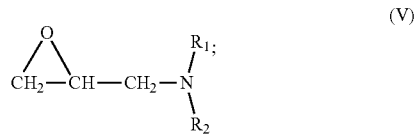

wherein, for formulas (I), (II) and (V), $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 4 carbon atoms, $A^-$ is an anion chosen from halogens, and, where applicable, A is a halogen.

Use for providing hydrophobicity may also be referred to as a method for increasing the hydrophobic properties of a substance by contacting it with at least one compound of formula (I), (II) or (V) as described herein.

When used for providing hydrophobicity, the compounds may react with other non-hydrophobic or less hydrophobic substances to provide increased hydrophobic properties thereof.

The compounds can be used in their pure forms or in compositions, such as aqueous compositions comprising at least one of said compounds or compositions in which at least one of said compounds is mixed with an organic solvent. Possible organic solvents include, for example, at least one hydrocarbon solvent compatible with those of the compounds of formula (I), (II), and (V) that are present in the composition. Suitable organic solvents include hydrocarbons comprising from 1 to 12 carbon atoms, such as hydrocarbons comprising a six membered ring, which may contain 6 delocalised π-electrons. The organic solvent may, for example, be a non-polar organic solvent, typically comprising form 5 to 12 carbon atoms, such as non-polar aromatic or aliphatic hydrocarbons. Examples of suitable organic solvents include, but are not limited to alcohols (methanol, ethanol, isopropanol), polar aprotic solvents (DMSO, DMF, DMA, or acetonitrile), aliphatic hydrocarbons (e.g. pentane, hexane, heptane, cyclopentane or cyclohexane), dichlormethane or other chlorinated solvents, or common aromatic solvents like benzene, chlorobenzene, toluene or different isomers of xylene. A mixture of different organic solvent may also be applied, such as any mixture of the classes of solvents or specific solvents disclosed above. It is also possible to use compositions comprising two or more of said compounds of formula (I), (II) and (V) as defined above without further additives, for example a mixture of compounds of formula (II) and (V) as defined above.

A further aspect of the invention relates to a composition comprising at least one compound chosen among compounds of formula (I) or formula (II), and mixtures thereof, and at least one further component, wherein $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 4 carbon atoms, $A^-$ is an anion chosen from halogens, and, where applicable, A is a halogen. Said further component may be water or at least one organic compound. Such an organic compound may, for example, be a compound of formula (V), particularly as defined above. The organic compound may also be an organic solvent or mixture of solvents. For compounds of formula (I), a dispersion or emulsion thereof in water is preferred. For compounds of formula (II), a composition further comprising a compound of formula (V) and/or another organic compound, such as an organic solvent as defined above, is preferred.

A composition as described above may be used as a hydrophobing composition. According to an embodiment the composition may be an aqueous composition such as an aqueous hydrophobing composition. In the field of paper and paper board making, compounds imparting hydrophobicity to the end product (such as paper and paper board) are usually referred to as sizing compounds or sizing agents. Compounds of formula (I), (II) and (V) as described above, and mixtures thereof, have been found useful as sizing agents and may be included in sizing compositions. A sizing composition of the invention may, for example, be an aqueous composition comprising at least one compound of formula (I), (II) or (V) as described above.

In the compositions the compound of formula (I), (II), (V), and mixtures thereof, particularly compounds of formula (I), function primarily as a compound providing increased hydrophobicity, i.e. as a sizing agent. While compounds of formula (II) and (V) may provide some hydrophobic character to paper and paper board, compounds of formula (II) and (V) have the ability, when subjected to water, to form compounds of formula (I).

According to yet a further aspect the invention relates to a process for manufacturing paper or paper board comprising providing an aqueous cellulosic suspension, dewatering the aqueous cellulosic suspension thereby providing a web of paper or paper board, the process comprising adding to the cellulosic suspension or to the web of paper or paper board a compound chosen among compounds of formula (I), formula (II), formula (V), and mixtures thereof, wherein $R_1$ and $R_2$, independently from each other, are chosen from hydrocarbons having from 1 carbon atom up to 30 carbon atoms, with the proviso that at least one of $R_1$ and $R_2$ are chosen among preferably aliphatic hydrocarbons having at least 4 carbon atoms, and, where applicable, A is a halogen.

Thus, the compound chosen among compounds of formula (I), formula (II), formula (V), and mixtures thereof may be added to the cellulosic suspension or the compound may be added to the web of paper or paper board. Alternatively, the process may comprise the addition of said components to both the aqueous cellulosic suspension and to the web of paper or paper board.

According to an embodiment of the process the compound chosen among compounds of formula (I), formula (II), formula (V), and mixtures thereof may be provided as a composition, such as an aqueous composition, prior to being applied in the process, such as being added to the aqueous cellulosic suspension or added to the web of paper or paper board. The composition and the aqueous composition may be referred to as a hydrophobing (sizing) composition and an aqueous hydrophobing (sizing) composition.

The embodiments disclosed in this application are not considered to be construed as limiting the gist of the present invention.

According to a variant concerning the embodiments including hydrophobic agent, composition, aqueous composition, method for producing a hydrophobing composition, use of the compounds, process for manufacturing paper or paper board and paper or paper board, said embodiments may relate to any one of compound of formula (I), (II), (V), and mixtures thereof. Hence, said embodiments may relate to compounds of formula (I), or relate to compounds of formula (II), or, relate to compounds of formula (V); or relate to compounds of any mixture comprising two different, or three different compounds of formula (I), (II) and (V).

The term hydrocarbon as used in this application relates to a moiety/group not containing hetero atoms. Thus, the term hydrocarbon relates to moiety/group only containing the atoms carbon and hydrogen. Thus, typically hydrocarbon relates to a group/chemical group/moiety consisting of carbon (one or more carbon atoms) and hydrogen atoms.

The hydrocarbon, can be straight, branched and may also contain one or more double bonds between carbon atoms. When a hydrocarbon contains at least one carbon-carbon double bond it is usually referred to as a unsaturated hydrocarbon. The carbon atoms of the hydrocarbon may be arranged so as to provide one or more ring structures, such as a hydrocarbon comprising one or more carbon rings to which hydrogen atoms are attached. A hydrocarbon comprising a carbon atom back-bone arranged in the form of one or more rings, may be referred to as a cyclic hydrocarbon. A hydrocarbon comprising one or more carbon ring structures may also comprise one or more carbon-carbon double bonds and can be referred to as a cycloalkene or a cyclic unsaturated hydrocarbon. Such carbon-carbon double bonds may be localised in the ring system or between carbon atoms not included in a ring system, or in both the ring system and other parts of the hydrocarbon. A cyclic hydrocarbon not comprising carbon-carbon double bonds may be referred to as a cycloalkane or cyclic saturated hydrocarbon.

The term aliphatic hydrocarbon as used herein refers to a hydrocarbon not containing any aromatic moieties. By aromatic moiety/moieties is meant a planar ring system obeying Hückel's rule, i.e. when the number of π-electrons of a carbon-carbon ring system equals 4n+2, where n is zero or a positive integer. Thus, an aromatic hydrocarbon may comprise planar ring systems having delocalised π-electrons of a number represented by 4n+2, where n is zero or a positive integer. A common aromatic system is represented by a ring system of six carbon atoms comprising 6 π-electrons, commonly referred to as benzene or benzol moiety. A hydrocarbon comprising aromatic moieties may be referred to as aryl or aralkyl (groups). In the context of this application aryl refers to any functional group or substituent derived from an aromatic ring such as phenyl, naphthyl, xylyl, consisting of carbon and hydrogen atoms. Aralkyl is understood as a hydrocarbon compound comprising at least one aromatic ring system to which aromatic ring system a non-aromatic hydrocarbon moiety is (covalently) attached.

According to an embodiment of the invention the hydrocarbons may be chosen among straight or branched alkyl or alkenyl.

In accordance with an embodiment applicable to all aspects of the present invention and regarding formula (I), and formula (II), per se and further to a method of producing the compound of formula (I), (II), and (V), and mixtures thereof, $R_1$ and $R_2$, independently from each other, are preferably chosen among hydrocarbons having from 1 carbon atom up to 30 carbon atoms, with the proviso that at least one of $R_1$ and $R_2$ are chosen among aliphatic hydrocarbons having at least 8 carbon atoms. Accordingly, at least one of $R_1$ and $R_2$ is a hydrocarbon having from 8 up to 30 carbon atoms.

According to an embodiment regarding the compounds of formula (I), and (II) per se, and further to a method of producing the compound of formula (I) and (II), and mixtures thereof, $R_1$ and $R_2$, independently from each other, are chosen among hydrocarbons having from 1 carbon atom up to 26 carbon atoms, with the proviso that at least one of $R_1$ and $R_2$ are chosen among aliphatic hydrocarbons having at least 8 carbon atoms. Here, at least one of $R_1$ and $R_2$ is a hydrocarbon having from 8 up to 26 carbon atoms.

According to other aspects of the present invention relating to a composition, method of producing a composition, the use of the compounds of formula (I), (II), (V), and mixtures thereof for providing hydrophobicity, alternatively, the use of formula (I), (II), (V), and mixtures thereof as a hydrophobing agent, a process for manufacturing paper or paper board, and paper, $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 4 carbon atoms. According to an embodiment, $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 8 carbon atoms. According to another embodiment, $R_1$ and $R_2$, independently from each other, are chosen among hydrocarbons having from 1 carbon atom up to 26 carbon atoms, with the proviso that at least one of $R_1$ and $R_2$ are chosen among preferably aliphatic hydrocarbons having at least 4 carbon atoms. According to another embodiment, $R_1$ and $R_2$, independently from each other, are chosen among hydrocarbons having from 1 carbon atom up to 26 carbon atoms, with the proviso that at least one of $R_1$ and $R_2$ are chosen among aliphatic hydrocarbons having at least 8 carbon atoms.

Hence, according to an embodiment of the invention, and common to all aspect/varieties of the present invention, $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 8 carbon atoms. Preferably, $R_1$ and $R_2$, independently from each other, are chosen among hydrocarbons having from 1 carbon atom up to 26 carbon atoms, with the proviso that at least one of $R_1$ and $R_2$ are chosen among preferably aliphatic hydrocarbons having at least 8 carbon atoms. Thus, according to the latter embodiment common to all aspect of the present invention, at least one of $R_1$ and $R_2$ is a hydrocarbon having from 8 up to 26 carbon atoms, According to yet another embodiment (common to all aspects) $R_1$ and $R_2$, independently from each other, are chosen among preferably aliphatic hydrocarbons having from 1 carbon atom up to 26 carbon atoms, with the proviso that at least one of $R_1$ and $R_2$ are chosen among preferably aliphatic hydrocarbons having at least 8 carbon atoms, i.e. at least one of $R_1$ and $R_2$ is a hydrocarbon having from 8 up to 26 carbon atoms, and chosen among straight or branched alkyl, alkenyl, aryl, or aralkyl hydrocarbons.

According to yet another embodiment applicable to all aspects/variants and other embodiment one of $R_1$ and $R_2$, or both, may be chosen among preferably aliphatic hydrocarbons having from 6, having from 8, having from 10, having from 12 carbon atoms, having from 14 carbon atoms or from 16 carbon atoms. Furthermore, one of $R_1$ and $R_2$, or both, may be chosen among preferably aliphatic hydrocarbons up to 28, up to 26, up to 24 or up to 22 carbon atoms. $R_1$ and $R_2$, or both, may be chosen among preferably aliphatic hydrocarbons having a number of carbon atoms of a number which is given by a combination of any of the lower numbers of carbon atoms (i.e. 6, 8, 10, 12, 14 or 16 carbon atoms) and any of the higher numbers of carbon atoms (i.e. 22, 24, 26 or 28 carbon atoms). For example, at least one of $R_1$ and $R_2$, or both $R_1$ and $R_2$, may be chosen among preferably aliphatic hydrocarbons having at least 10 carbon atoms or at least 16 carbon atoms, such as from 10 to 24 carbon atoms or from 16 to 24 carbon atoms.

According to yet another embodiment applicable to all aspects/variants and other embodiments, any one of compounds of formula (I), (II), (V), and mixtures thereof, suitably compounds of formula (I), may be defined as indicated above, however, with the additional feature that the total amount of carbon atoms present in $R_1$ and $R_2$ may be more than 12 carbon atoms, more than 14 carbon atoms, more than 16 carbon atoms, more than 18 carbon atoms, more than 20 carbon atoms. It has been found that the dispersibility/emulsifiablility, such as self-dispersibility/self-emulsifiablility, specifically compounds of formula (I), tend to correlate with the amount of carbon atoms in substituents $R_1$ and $R_2$ such as the total amount of carbon atoms in substituents $R_1$ and $R_2$. More specifically, the dispersibility increases with increasing amount of total amount of carbon atoms in substituents $R_1$ and $R_2$.

It has been found that compounds of the invention, particularly compounds of formula (I), easily can be emulsified/dispersed in an aqueous phase, in many cases even without the addition of further compounds facilitating the formation of free surface area (commonly referred to as dispersing/emulsifying agents).

Compound chosen among compounds of formula (I), (II), (V), and mixtures thereof, may be added to a cellulosic suspension, alternatively to a web of paper or paper board as an aqueous emulsion/dispersion, but may also be added per se to a cellulosic suspension or to a web of paper or paper board, without the need of first being emulsified/dispersed in an aqueous phase.

According to a further embodiment common to all aspects/variants of the present invention the hydrocarbon group which is defined to contain at least 4 carbon atoms, alternatively at least 8 carbon atoms, is chosen among straight hydrocarbons (including saturated and unsaturated hydrocarbons), or may be chosen from saturated straight (suitably non-branched) hydrocarbons, alternatively, may be chosen from unsaturated straight (suitably non-branched) hydrocarbons.

According to another embodiment common to all aspects of the present invention, $R_1$ and $R_2$, independently from each other, are chosen among preferably aliphatic hydrocarbons having from 8 carbon atoms up to 30 carbon atoms, suitably from 8 carbon atoms up to 26 carbon atoms, suitably from 8 carbon atoms up to 22 carbon atoms. According to yet another embodiment common to all variants/aspects of the invention, $R_1$ and $R_2$, independently from each other, are chosen among straight (non-branched) aliphatic hydrocarbons having from 8 carbon atoms up to 26 carbon atoms, suitably from 8 carbon atoms up to 24 carbon atoms, suitably from 8 carbon atoms up to 22 carbon atoms. The low level of the number of carbon atoms in the above ranges relating to the hydrocarbons of both $R_1$ and $R_2$ (independently from each other) are from 9, or, 10, or 11, or 12, or 14 carbon atoms. Thus, both $R_1$ and $R_2$, independently from each other, may be chosen from hydrocarbons from e.g.: 9 to 30 carbon atoms, 8 to 28, 9 to 28, 10 to 30, 10 to 28, 11 to 30, 11 to 28, 12 to 30, 12 to 28, 8 to 26, 10 to 26, 12 to 26, 8 to 24, 10 to 24, 12 to 24, 8 to 22, 10 to 22, 12 to 22.

Throughout the application the wording chosen among may be replaced by the language "selected from the group comprising", alternatively, replaced by the language "selected from the group consisting of".

Compounds of formula (I) may be referred to as quaternary ammonium containing compounds, alternatively, may be referred to as azetidinium compounds or compounds comprising an azetidinium functionality. Azetidine (or aza-cyclobutane/trimethylene imine) is a heterocyclic organic compound comprising a four membered ring of three carbon atoms and a nitrogen atom, thus, azetidinium or azetidinium compounds comprise a four membered ring system comprising a positively charged nitrogen atom. The nitrogen atom in formula (I) is positively charged, thus, rendering a positively charged organic compound. This positive charge is typically balanced by the presence of anionic compounds and/or atoms, specifically in compositions comprising water, i.e. aqueous compositions comprising the positively charged organic azetidinium compound. The compound of formula (I) may be present as a salt.

Compounds of formula (II) may by be referred to as a halohydrin or haloalcohol. Halohydrins are organic compounds comprising a carbon atom having a halogen substituent and an adjacent carbon atom having a hydroxyl substituent.

Compounds of formula (I), (II) and (V), are typically formed by reacting secondary amines of formula (III) and epihalohydrins of formula (IV).

According to one reaction scheme (A) the secondary amine of formula (III) and epihalohydrin of formula (IV) are converted to predominantly compounds of formula (I) in essentially one reaction step. According to this scheme (A) the secondary amine and epiholohydrin react in an aqueous reaction medium. Typically, scheme (A) comprises providing the secondary amine in liquid form and mixing with epihalohydrin and water, preferably at an elevated temperature, such as above about 70° C., suitably between a temperature of from 70 up to 120° C., suitably from 80 up to 110° C., for example during a time from 30 minutes up to 20 hours.

According to another reaction scheme (B), compounds of formula (I), (II) and (V) are formed by reacting a secondary amine of formula (III) and epihalohydrin of formula (IV) in a reaction medium comprising an organic solvent. This reaction step may be referred to as the first step of scheme (B). Typically, the reaction medium where the reaction of the secondary amine and epihalohydrin takes place is essentially free from constituents/components (such as water) reacting with epohalohydrin to form by products which have a negative impact on the rate of conversion to the desired products. If water is present during the reaction of the secondary amine and epihalohydrin, the latter compound (epihalohydrine) may react with water under formation of halogen substituted alcohols (excluding compounds of formula (II), both including dichloropropanol (DCP) and chloropropanediol (CPD)). Preferably, the reaction medium is essentially free from water, or, free from water. Alternatively, the reaction medium comprises a solvent which is essentially free from water, or, free from water. By essentially free from water is meant an amount of water in the reaction medium which at the end of the first step has yielded an acceptable amount of halogen substituted alcohols such as DCP and CPD. Suitably, the reaction medium is free from water or any other compounds which are capable to transform/convert the epihalohydrin to unwanted compounds including halogen substituted alcohols such as DCP and CPD. By free from water is more specifically meant a reaction medium comprising less than 1% by weight of water based on total composition, such as less than 0.1% by weight. The reaction medium may also essentially consist of, or consist of, at least one organic solvent, such as at least one hydrocarbon solvent capable of generating a satisfactory yield with respect to formula (I) and (II), and to some extent (V). Suitable organic solvents are hydrocarbons comprising from 1 to 12 carbon atoms, said hydrocarbons preferably comprises a six membered ring, which may contain 6 delocalised π-electrons. Suitably, the organic solvent is a non-polar organic solvent, typically comprising form 5 to 12 carbon atoms, such as non-polar aromatic hydrocarbons. Examples of suitable organic solvents include, but are not limited to alcohol (methanol, ethanol, isopropanol), dichlormethane, chlorinated solvents, cyclopentane, hexane, cyclohexane, benzene and toluene. Benzene and toluene may be applied as organic solvent. A mixture of different organic solvent may also be applied, such as any mixture of the classes of solvents or specific solvents disclosed above.

The reaction of a secondary amine formula (III) and a halohydrin of formula (IV) generates compounds of formula (I), or a mixture of formula (I), (II), and (V), depending on the scheme of reaction. Epoxyamines of formula (V) are typically formed when applying a (reaction) medium which is essentially free from constituents/components reacting with epohalohydrin to from compound reducing the yield of compounds of formula (II) and thus ultimately compounds of formula (I).

The first step of scheme (B) is suitably conducted at elevated temperatures in the range of from about 10 to about 300° C., such as from about 50 to about 200° C., and from about 10 to about 1000 minutes, or, from about 30 to about 300 minutes.

As already disclosed compounds of formula (I), i.e. azetidinium (or azetidinium compounds) may be formed during essentially one stage in scheme (A). In reaction scheme B the yield of azetidinium can be increased by adding water to the reaction mixture obtained from the first step. Typically, the reaction medium comprising compounds of formula (I), (II) and (V) comprise a very low amount of halogen substituted organic compounds such as halogen substituted alcohols (such as DCP and CPD), or preferably negligible amount of halogen substituted organic compounds. Suitably, prior to the addition of water to the reaction medium (from the first step) the reaction medium may be essentially free from halogen substituted organic compounds, or, the reaction medium is free from halogen substituted organic compounds. While it may be favourable to add water to the reaction mixture from the first step compounds of formulas (I), (II) and (V), said compounds may be isolated from the reaction medium and mixed with water to further react to compounds of formula (I). Compounds of formula (II) and (V), i.e. the halohydrins and epoxyamines, react with water at elevated temperatures thereby yielding azetidinium compounds of formula (I). Thus, the yield of azetidinium is increased by subjecting compounds of formula (II) and (V) to water. This step where compounds of formula (II) and (V) are transformed to azetidinium compounds of formula (I) is referred to as the second step.

The second step of scheme (B) is suitably conducted at elevated temperatures in the range of from about 20 to about 150° C., such as from about 60 to about 100° C., and preferably from about 10 to about 200 minutes, or, from about 20 to about 60 minutes.

According to still another reaction scheme (C), the first step is performed as in reaction scheme (B) with the exception that no solvent is present. Thus, the secondary amine of formula (III) and the epihalohydrin of formula (IV) are mixed in the absence of any further solvent. In all other aspects the conditions of reaction scheme (B) are applicable. Likewise, the second step of adding water to the reaction mixture obtained is performed as in reaction scheme (B).

The yield of azetidinium based on secondary amine or epihalohydrin may be more than 60%, more than 70%, more than 80% more than 88%, such as more than 90%, preferably when applying schemes (B) or (C). Furthermore, the formation of halogen substituted organic compounds, such as DCP and CPD, when applying scheme (B) is reduced, alternatively may be essentially fully suppressed.

If compounds like DCP and CPD are formed to unacceptable extent, they may be removed from the reaction medium or the end products by applying suitable additional process stages, such as ion exchange, electrodialysis, enzymatic treatment, and extraction with carbon dioxide, such as super critical carbon dioxide.

Thus, according to an embodiment there is provided a composition comprising a compound of formula (I), where $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 8 carbon atoms, and A is a halogen; and wherein the composition is essentially free, preferably free, from halogen substituted organic compounds (such as DCP and CPD).

As understood herein, and which is common in the art, secondary amines relate to organic amines comprising a basic nitrogen atom with two lone electron pairs such as derivatives of ammonia where two hydrogen atoms have been substituted by hydrocarbon groups. Primary amines are derived from ammonia where one hydrogen atom is substituted by a hydrocarbon group. The secondary amines may be obtained from primary amines.

At least one, or both the hydrocarbon groups of the secondary amines, may be derived from fats and oils from plants and animals. The fats and oil are usually provided in the form of triglycerides. Depending on the origin of the fat or oil the triglycerides comprise characteristic fatty acids. The fatty acids derived from triglycerides are typically mono carboxylic fatty acid residues comprising from around 6 up to 24 carbon atoms. The carboxylic fatty acid may be provided as saturated carboxylic fatty acids, i.e. the hydrocarbon tail does not contain C—C double bonds, or as unsaturated fatty acid residues typically comprising one up to three C—C double bonds in the hydrocarbon "fatty" tail. Suitable fatty carboxylic acids for providing secondary amines may be derived from palm oil, soybean oil, rapeseed oil, sun flower oil, peanut oil, cotton seed, palm kernel oil, olive oil, and fatty carboxylic acids derived from animal sources such as lard and fats form cattle. Frequent carboxylic acids derived from natural resources include carboxylic acids comprising from 8 up to 24 carbon atoms, such as saturated fatty acids e.g. caprylic fatty acid (C8), capric fatty acid, lauric fatty acid, myristic fatty acid, palmitic fatty acid, stearic fatty acid, arachidic fatty acid, behenic fatty acid and lignoceric fatty acid; and saturated fatty acids including polyunsaturated fatty acids such as palmitoleic fatty acid, oleic fatty acid (C18:1 [double bond]), linoleic fatty acid (C18:2), linolenic fatty acid (C18:3). Usually, fatty acids derived from natural sources, such as any of the natural sources indicated in this application, e.g. fatty acids derived from palm oil, comprise fatty acids of varying numbers of carbon atoms. Thus, if not further treated (classified), fatty acids from a specific type of plant (such as palm, soybean, rapeseed, etc) comprise a variety of fatty acids differing in the number of carbon atoms and sometimes also in the number of carbon-carbon double bonds. Accordingly, secondary amines derived from fatty acids from natural resources tend to comprise secondary amines having different hydrocarbon substituents derived from the different fatty acids of the respective plant.

In addition to the secondary amine, also a epihalohydrin of formula (IV) is present in the reaction medium. The epihalohydrin may be chosen among epihalohydrins comprising any halogen from Group 17 (IUPAC) of the periodic table, notably fluorine (F), chlorine (Cl), bromine (Br), iodine (I), and astatine (At). Suitably, epihalohydrins are chosen among epichlorohydrin, epibromohydrin, and epoiodohydrin. Preferred epihalohydrins are chosen among epichlorohydrin, epibromohydrin. Epichlorohydrin is preferred.

Similarly, A in formula (I), (II) and (V) may be any halogen such as fluorine, chlorine, bromine, iodine and astatine, among which chlorine is preferred.

Depending on the length of the hydrocarbon substituents $R_1$ and $R_2$ in formulas (I), (II), and (V), the compounds of formulas (I), (II), and (V) may, at ambient temperature (such as ranging from 0 to 30° C.), be provided in the form of a liquid or in solid form (such as a deformable solid state, e.g. wax) or in a any form/state between liquid and solid.

In an embodiment a sizing composition of the invention may be a composition essentially consisting of a compound chosen among compounds of formulas (I), (II), (V), and mixtures thereof. In this embodiment, the amount of compounds chosen among compounds of formulas (I), (II), (V), and mixtures thereof, such as compounds chosen among compounds of formulas (I), (II), or, compounds of formula (I), is more than 90% based on total composition, suitably more than 95%, and typically more than 98% based on total composition. Such sizing compositions may be homogenised at the location of use, by homogenising/dispersing/emulsifying the composition in the presence of an aqueous phase prior to the addition to the paper making process (addition to a cellulosic suspension and/or addition to a formed web of cellulosic matter subsequent dewatering). The composition may be heated before, during or subsequent homogenisation.

According to a further embodiment the sizing agent comprising (I), (II), (V), and mixtures thereof, suitably a sizing agent consisting essentially of (I), (II), (V), and mixtures thereof, is added as such in a process for manufacturing paper such as being added to a cellulosic suspension or to a web of paper and paper board, or both.

According to an embodiment the compound chosen among compounds of formulas (I), (II), (V), and mixtures thereof may in a process for manufacturing paper or paper board be applied on the paper web or paper board web so as to provide additional hydrophobicity to the surface of the web. When compounds of formulas (I), (II), (V), and mixtures thereof are applied to the surface of a paper or paper board web said compounds may be provided in the form of aqueous compositions, such as a size press liquor, typically further comprising starch, such as anionic, non-ionic, cationic or amphoteric starch. Compounds of formulas (I), (II), (V), and mixtures thereof applied to the surface of a web of paper or paper board may be referred to as surface sizing agents. A surface sizing composition may comprise further substances, such as, for example, (e.g. chalk, precipitated calcium carbonate, kaolin, titanium dioxide, barium sulphate or gypsum), optical brighteners, biocides, strength agents for paper, fixing agents, antifoams, retention aids, crosslinkers (e.g. zirconium compounds), insolubilisers, defoamers, and/or drainage aids. The amounts of compounds of formulas (I), (II), (V), and mixtures thereof applied to the surface of paper web may, for example, be from 0.005 to 1.0 $g/m^2$ or from 0.01 to 0.5 $g/m^2$.

According to an embodiment the sizing composition comprises a compound of formula (I), or a composition comprising a sizing agent being a compound of formula (I), wherein $R_1$ and $R_2$, independently from each other, are chosen among hydrocarbons having from 1 carbon atom up to 30 carbon atoms, with the proviso that at least one of $R_1$ and $R_2$ are chosen among preferably aliphatic hydrocarbons having at least 4 carbon atoms, $A^-$ is an anion chosen from halogens, and, A is a halogen.

According to a further embodiment there is provided a composition comprising any one of the compounds of formulas (I), (II), (V), and mixtures thereof also comprising other conventional sizing agents such as rosin-based sizing agents and cellulose reactive sizing agent including ketene dimers, ketene multimers, organic isocyanides, carbamoyl chlorides and acid anhydrides, such as alkyl and alkenyl succinic anhydrides, e.g. iso-octadecenyl succinic anhydride, iso-octadecyl succinic anhydride, n-hexadecenyl succinic anhydride, dodecenyl succinic anhydride, decenyl succinic anhydride, octenyl succinic anhydride, tri-isobutenyl succinic anhydride, 1-octyl-2-decenyl-succinic anhydride and 1-hexyl-2-octenyl-succinic anhydride.

According to an embodiment the composition may be provided in the form of an aqueous composition. In this regard a sizing composition may be referred to as an aqueous sizing composition. Thus, an aspect of the invention concerns an aqueous composition, such as an aqueous sizing composition, comprising a compound chosen among compounds of formula (I), (II), (V), and mixture thereof. According to an embodiment the aqueous sizing composition, suitably an aqueous sizing composition comprising a compound of formula (I), or an aqueous sizing composition comprising a sizing agent essentially selected from compounds of formula (I), is essentially free (or free) from compounds/agents which facilitate the formation of free (particle) surface area. Compounds increasing the formation of free surface are usually surface active compounds comprising at least a hydrophilic moiety and at least a hydrophobic moiety. Even if the sizing composition and aqueous sizing composition suitably may not contain additional compounds facilitating the formation of an emulsion or dispersion, the sizing compositions and aqueous sizing compositions may comprise compounds facilitating the formation of an emulsion or dispersion. Suitable dispersion/stabilising agents may include surfactants, electrolytes and polyelectrolytes. Polyeletrolyes may be anionic, cationic, amphoteric or non-ionic. Polyelectrolytes may be selected from organic and inorganic compounds, may be derived from natural or synthetic sources and can be linear, branched or cross-linked. Polelectrolytes are suitably water-dispersible and/or water-soluble. Polyelectrolytes stemming from natural sources include (or be derived from) polysaccharides, such as starches, guar gum, celluloses, chitins, chitosans, glycans, galactans, xanthan gums, pectins, mannans, dextrins, preferably starches and gums. Suitable starches include starches deriver form potato, corn, wheat, tapioca, rice, waxy maize, barley. Synthetic polyelecrolytes may include chain-growth polymers, e.g. addition polymers, step-growth polymers. Synthetic chain-growth polyelectolytes include vinyl addition polymers such as acrylate-, acrylamide-, and vinylamide-based polymers. Suitable step-growth polymers include condensation polymers, such as condensates of an aldehyde and polyurethanes. The polyelectrolytes may contain native chemical groups comprising charges, such as groups which are bound to the monomers. Alternatively, the polyelectrolytes are rendered charged or are provided with additional charges by the introduction of charges moieties (chemical groups) after the formation of the polymer. The charge of some polyelectrolytes may also vary based on the type of solvent, and based on the pH of an aqueous solvent.

Examples of suitable anionic groups, i.e. groups that are anionic or rendered anionic in an aqueous phase, include silanol, aluminosilicate, phosphate, phosphonate, sulphate, sulphonate, sulphonic and carboxylic acid groups as well as salts thereof, usually ammonium or alkali metal (generally sodium) salts. Preferred groups of additional compounds present in the aqueous composition are charged polysaccharides, specifically starch, and charged acrylamide-based polymers.

Suitably the amount of compound of formula (I), or the sum of any of the compounds (I), (II), and (V), applied as such or comprised in a composition applied, such as an aqueous composition, either added to the cellulosic suspension to be drained on a wire to form paper, or applied to the surface of a cellulosic sheet or web as a surface size, usually at the size press, is from 0.01 to 1.0% by weight, based on dry cellulosic suspension and optional fillers, preferably from 0.05 to 0.5% by weight, where the dosage is mainly dependent on the quality of the pulp or paper to be sized and the level of sizing desired.

A further aspect of the invention relates to the use of a compound according to formula (I) (II), (V), and mixtures thereof for providing hydrophobicity. Suitably the compounds of formula (I), (II), (V), and mixtures thereof are used as hydrophobing (sizing) agents. According to an embodiment compounds of formula (I), (II) and (V), preferably compounds of formula (I), are used for providing hydrophobicity of paper or paper board and may then be referred to as sizing agents.

The compounds of formula (I), (II), (V), and mixtures thereof, as such or in the form of a composition, such as a sizing composition or aqueous sizing composition, can be used in conventional manner in the production of paper using any type of cellulosic fibres and they can be used both for surface sizing and internal sizing.

The compounds of formula (I), (II), and (V), and mixtures thereof may be used in conjunction with additional non-cellulosic performance chemicals such as drainage and retention aids and additional sizing agents. Examples of suitable drainage and retention aids include organic polymers, inorganic materials, e.g. anionic microparticulate materials, e.g. siliceous materials such as like colloidal silica-based particles, such as siliceous material comprising silica-based material, montmorillonite/bentonite, and combinations thereof. The term "drainage and retention aid", as used herein, refers to one or more additives which, when being added to an aqueous cellulosic suspension, give better drainage and/or retention than is obtained when not adding said one or more additives.

Examples of suitable organic polymers include anionic, amphoteric and cationic starches; anionic, amphoteric and cationic acrylamide-based polymers, including essentially linear, branched and cross-linked anionic and cationic acrylamide-based polymers; as well as cationic poly(diallyldimethyl ammonium chloride); cationic polyethylene imines; cationic polyamines; cationic polyamideamines and vinylamide-based polymers, melamine-formaldehyde and urea-formaldehyde resins. Suitably, the drainage and retention aid comprises least one cationic or amphoteric polymer, preferably cationic polymer. Cationic starch and cationic polyacrylamide are particularly preferred polymers and they can be used singly, together with each other or together with other polymers, e.g. other cationic and/or anionic polymers. The weight average molecular weight of the polymer is suitably above about 1,000,000 and preferably above about 2,000,000. The upper limit of the weight average molecular weight of the polymer is not critical; it can be about 50,000,000, usually about 30,000,000 and suitably about 25,000,000. However, the weight average molecular weight of polymers derived from natural sources may be higher.

Silica-based particles, i.e. particles based on $SiO_2$ or silicic acid, are usually supplied in the form of aqueous colloidal dispersions, so-called sols. Examples of suitable silica-based particles include colloidal silica and different types of polysilicic acid, either homopolymerised or co-polymerised. The silica-based sols can be modified and contain other elements, e.g. aluminum, boron, nitrogen, zirconium, gallium, titanium and the like, which can be present in the aqueous phase and/or in the silica-based particles. Examples of suitable silica-based particles of this type include colloidal aluminum-modified silica and aluminum silicates. Mixtures of such suitable silica-based particles can also be used. Examples of suitable anionic silica-based particles include those having an average particle size below about 100 nm, preferably below about 20 nm and more preferably in the range of from about 1 to about 10 nm. As conventional in the silica chemistry, the particle size refers to the average size of the primary particles, which may be aggregated or non-aggregated. The specific surface area of the silica-based particles is suitably above about 50 $m^2/g$ and preferably above about 100 $m^2/g$. Generally, the specific surface area can be up to about 1700 $m^2/g$. The specific surface area is measured by means of titration with NaOH in a well known manner, e.g. as described by G. W. Sears in Analytical Chemistry 28 (1956): 12, 1981-1983 and in the U.S. Pat. No. 5,176,891. The given area thus represents the average specific surface area of the particles. Further examples of suitable silica-based particles include those that are present in a sol having an S-value in the range of from 5 to 50%. The S-value can be measured and calculated as described by Iler & Dalton in J. Phys. Chem. 60 (1956), 955-957. The S-value indicates the degree of aggregation or microgel formation and a lower S-value is indicative of a higher degree of aggregation.

According to another aspect the present invention also relates to a process for manufacturing paper or paper board comprising providing an aqueous cellulosic suspension, dewatering the aqueous cellulosic suspension thereby providing a web of paper or paper board, the process comprising adding a compound chosen among compounds of formula (I), (II), (V), and mixtures thereof to the aqueous cellulosic suspension and/or to a web of paper or paper board, where $R_1$ and $R_2$, independently from each other, are chosen from hydrocarbons having from 1 carbon atom up to 30 carbon atoms, with the proviso that at least one of $R_1$ and $R_2$ are chosen among aliphatic hydrocarbons having at least 4 carbon atoms, and, where applicable, A is a halogen.

The term "paper", as used herein, of course include not only paper and the production thereof, but also other cellulosic sheet or web-like products, such as for example board and paperboard, and the production thereof. The process can be used in the production of paper from different types of aqueous suspensions of cellulosic fibers and the suspensions should suitably contain at least about 25% by weight and preferably at least about 50% by weight of such fibers, based on dry substance. The suspension can be based on fibers from chemical pulp such as sulphate, sulphite and organosolv pulps, mechanical pulp such as thermo-mechanical pulp, chemo-thermomechanical pulp, refiner pulp and groundwood pulp, from both hardwood and softwood, and can also be based on recycled fibers, optionally from de-inked pulps, and mixtures thereof. The suspension may contain mineral fillers, such as conventional fillers including kaolin, china clay, titanium dioxide, gypsum, talc and natural and synthetic calcium carbonates such as chalk, ground marble and precipitated calcium carbonate. The pH of the suspension, the stock, can be within the range of from about 3 to about 10. The pH is suitably above about 3.5 and preferably within the range of from about 4 to about 9.4 to 8.

The process for manufacturing paper or paper board may also comprise the addition of a siliceous material to the aqueous cellulosic suspension. Suitable siliceous material comprises any of the siliceous material disclosed in this application.

The process for manufacturing paper or paper board may also comprise the addition of a siliceous material to the aqueous cellulosic suspension and a cationic polyelectrolyte.

The process for manufacturing paper or paper board may also comprise the addition to the aqueous cellulosic suspension of a drainage and retention aids comprising siliceous material and cationic polyelectrolyte, such as cationic polysaccharide, e.g. starch, and cationic acrylamide-based polymer.

The compounds of formula (I), (II), (V), and mixtures thereof, and compositions comprising said compounds are useful in the manufacture of paper from an aqueous cellulosic suspension that has a high conductivity. The conductivity of the suspension that is dewatered on the wire can be within the range of from 0.3 mS/cm to 10 mS/cm. According to this invention, good results can be achieved when the conductivity is at least 2.0 mS/cm, notably at least 3.5 mS/cm, particularly at least 5.0 mS/cm and even at least 7.5 ms/cm. Conductivity can be measured by standard equipment such as, for example, a WTW LF 330 instrument supplied by Christian Berner. The values referred to above are suitably determined by measuring the conductivity of the cellulosic suspension that is fed into or present in the headbox of the paper machine or, alternatively, by measuring the conductivity of white water obtained by dewatering the suspension. High conductivity levels mean high contents of salts (electrolytes) which can be derived from the materials used to form the stock, from various additives introduced into the stock, from the fresh water supplied to the process, etc. Further, the content of salts is usually higher in processes where white water is extensively recirculated, which may lead to considerable accumulation of salts in the water circulating in the process.

According to yet another aspect the invention pertains to paper and paper board obtainable/obtained by a process as disclosed in this application. Paper according to the invention can be used in numerous applications, such as packaging paper, printing (fine paper).

The invention is further illustrated in the following examples which, however, are not intended to limit the same. Parts and % relate to parts by weight and % by weight, respectively, unless otherwise stated.

EXAMPLE 1

Azetidinium compounds of formula (I) were produced according to the following general reaction schemes:

Reaction Scheme (A):

A fatty dialkyl amine derived from hydrogenated tallow ($C_{16}/C_{18}$) (0.2 mol) was melted at +90° C. in a glass-reactor equipped with a stirrer and reflux condenser. To this melt epichlorohydrin (16 ml; 0.2 mol) and distilled water (3.65 ml; 0.2 mol) were added and the mixture was kept at +90° C. for 16 h. GC-MS and $^{13}$C-NMR analysis showed that all epichlorohydrin had been consumed. LC-MS analysis of the mixture showed that azetidinium was a major product. However, further LC-MS and GC-MS analysis also showed that all starting material (fatty dialkyl amine) had not been consumed and that epichlorohydrine derived adducts such as DCP and CPD also were formed.

Reaction Scheme (B):

To a solution of the fatty amine (0.1 mol) in xylene as solvent was added epichlorohydrin (0.1 mol). The mixture was heated to reflux and the reaction progress was monitored by LC-MS (starting material and product) and GC-MS (epichlorohydrin) every 15 minutes. If necessary, extra additions of epichlorohydrin in portions of 0.01 mol were added in order to achieve full conversion. For fatty amines possessing longer R-groups (C16-C22) the reaction was completed after 2-3 h and for fatty amines possessing shorter R-groups (C8-C14) the reaction was complete after 0.5-2 h. When all fatty amine were consumed according to LC-MS the reaction mixture was cooled to room temperature and the organic liquids were evaporated using vacuum and heat. After evaporation a solid/liquid composition (below referred to as composition x) was obtained. LC-MS and $^{13}$C-NMR analysis showed that the main components of composition x were chlorohydrins of formula (II) and epoxyamine of formula (V). The longer fatty amines yielded a white-yellowish solid residue while the shorter fatty amines afforded a yellowish oil.

Reaction Scheme (C):

To a round-bottom flask containing the fatty dialkylamine (0.1 mol) was added epichlorohydrine (0.2 mol) with a syringe pump and the remaining mixture was heated to 90° C. After complete comsumption of the dialkyl amine (analysis by LC-MS) the excess epichlorohydrine was removed by vacuum distillation. The remaining liquid/solid depending on what fatty dialkylamine was used (see above) was collected and analyzed with LC-MS, $^{13}$C-NMR as described above.

In a further step the composition x comprising chlorohydrin and epoxyamine was mixed with water and heated to around 90° C. After about 30 minutes more than 90% of the initial amount of fatty amine was converted to azetidinium.

The following azetidinium compounds were produced according to scheme (B):

Azetidinium compounds of the following formula:

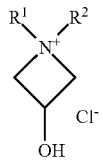

where:
R1=R2=C6H13, referred to as compound No 1
R1=R2=C8H17, referred to as compound No 2
R1=R2=Benzyl (C7H7), referred to as compound No 3
R1=R2=R-groups derived from coconut oil (predominately C12/C14), referred to as compound No 4

And the azetidinium compounds of formula:

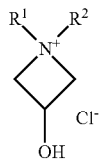

used below for sizing paper sheets and denoted No 5, No 7, and No 8, where:
No 5: $R_1=R_2=C_{10}H_{21}$
No 7: $R_1$ and $R_2$=mixture of hydrocarbons derived from hydrogenated tallow (predominantly $C_{16}$ and $C_{18}$)
No 8: $R_1=CH_3$, $R_2$=mixture of hydrocarbons derived from tallow (predominantely $C_{16}$ and $C_{18}$)
No 9: $R_1$ and $R_2$=mixture of hydrocarbons derived from rape-seed oil (predominantly $C_{20}$ and $C_{22}$)

EXAMPLE 2

Additionally, compound denoted No 6, disclosed in The Chinese paper "Synthesis and application of fatty amide sizing agent", M Ye-hong et. al., Zaozhi Huaxuepin (2010), 22 (Suppl.), Nanjing Forestry University, pp 36-41

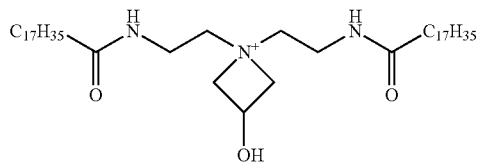

was prepared according to the disclosure in said Chinese document. A dispersion of compound No 6 was formed by dispersing compound No 6 in water.

EXAMPLE 3

Formation of aqueous sizing compositions comprising sizing agents (denoted No 5, No 6, No 7, No 8):

Aqueous dispersions of the compounds No 5, No 6 and No 8 as indicated above were formed by dispersing the compounds in water without the addition of additional compounds. The sizing agent was present in the aqueous dispersion in an amount of 8 to 10% by weight based on total composition.

EXAMPLE 4

As a reference, a sizing dispersion comprising a keten dimer, AKD (Eka DR28HF) was also prepared and used in the sizing tests below. The AKD was present in an amount of about 20% by weight based on total composition.

EXAMPLE 5

The sizing efficiency (Cobb-60) of the above dispersions was evaluated by measuring the sizing efficiency according to the standard method Tappi T441. Paper sheets were prepared according to the standard method SCAN-C26:76.

Paper sheets were prepared according to a process in which the dispersions were added to an aqueous cellulosic suspension of a consistency of 0.5% comprising 80% hardwood and 20% soft wood bleached kraft pulp based on total cellulosic fibres. The dispersions were added in amounts of 0.5, 1.0 and 2.0 kg/t, calculated as sizing agent and based on the weight of dry cellulosic suspension. A retention system was used comprising 6 kg/t of cationic potato starch (Perlbond 970, Lyckeby) and 0.5 kg/t of silica sol (NP 442, Eka Chemicals AB), calculated as dry substances on dry cellulosic suspension.

Cobb-60 values were measured and the results are presented in Table 1, in which the dosage refers to the amount of active compound (No. 5, 6, 7 or 8, or AKD) per tonne paper produced. A lower Cobb value means that a lower amount of water was absorbed and therefore better sizing was achieved.

TABLE 1

| Sizing agent | Sheet # | Sizing dosage/ [kg/ton] | Cobb/[g/m$^2$] |
| --- | --- | --- | --- |
| Blank | 0 | 0.0 | 157 |
| No 6 | 1 | 0.5 | 116 |
| No 6 | 2 | 1.0 | 29 |
| No 6 | 3 | 2.0 | 21 |
| No 5 | 4 | 1.0 | 124 |
| No 5 | 5 | 2.0 | 128 |
| Lab. ref. AKD (Eka DR28HF) | 8 | 0.5 | 24 |
| Lab. ref. AKD (Eka DR28HF) | 9 | 1.0 | 21 |
| Lab. ref. AKD (Eka DR28HF) | 10 | 2.0 | 20 |
| No 7 | 11 | 0.5 | 27 |
| No 7 | 12 | 1.0 | 22 |
| No 7 | 13 | 2.0 | 20 |
| No 8 | 14 | 1.0 | 138 |
| No 8 | 15 | 2.0 | 134 |

EXAMPLE 6

Surface sizing formulations were prepared from compounds 6, 7 and 9 by dispersion them into water to a concentration of approximately 5-15% solids. The sizing effect of the formulations were tested as described below on a test paper being a non-sized testliner grade from mixed waste, having a basis weight of 140 g/m$^2$ and a liquid absorption of 34%.

The treatment of the test paper was carried out on a laboratory size press from Mathis, Zürich, type HVF. The size liquor used was a solution of 8 parts by weight of dry oxidized potato starch (Perfectamyl P 255 SH from AVEBE)

and 0.05-1 parts of the compounds 6, 7 or 9, made up to 100 parts with water. The size press operation temperature was about 50-55° C.

The surface-sized papers were dried on a drying cylinder at 80° C. for approximately 2 minutes followed by drying in an oven for 10 minutes at about 105° C. Before the sizing test, the paper was conditioned for 12-18 hours at 23° C. and 50% r.h.

To assess the degree of sizing of the surface-sized papers, the Cobb values according to DIN 53122 were determined. The value is defined as the water absorption of a paper sheet in the course of a wetting time of 60 seconds, stated in g/m². The lower the Cobb value, the better is the degree of sizing of the treated papers.

The results are shown in Table 2, in which the dosage refers to the amount of active compound (No. 6, 7 or 9) per tonne paper produced.

TABLE 2

| Sizing agent | Sheet # | Sizing dosage/ [kg/ton] | Cobb/[g/m²] |
|---|---|---|---|
| Blank | 0 | 0 | 135 |
| No 7 | 1 | 0.5 | 87 |
| No 7 | 2 | 0.75 | 48 |
| No 7 | 3 | 1 | 32 |
| No 7 | 4 | 2 | 23 |
| No 9 | 5 | 0.3 | 96 |
| No 9 | 6 | 0.5 | 52 |
| No 9 | 7 | 0.75 | 26 |
| No 6 | 8 | 0.1 | 116 |
| No 6 | 9 | 0.2 | 49 |
| No 6 | 10 | 0.5 | 23 |

The invention claimed is:

1. A compound according to formula (I)

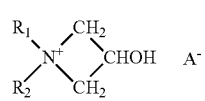
(I)

wherein each of $R_1$ and $R_2$, independently from each other, is a hydrocarbon having from 16 carbon atoms up to 30 carbon atoms and up to 30 carbon atoms, and A is a halogen; or a compound according to formula (II)

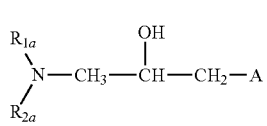
(II)

wherein each of $R_{1a}$ and $R_{2a}$, independently from each other, is an aliphatic hydrocarbon having at least 16 carbon atoms, and A is a halogen; or a mixture of compounds of formula (I) and formula (II).

2. A method for producing a compound or a mixture of compounds chosen among compounds of formula (I), formula (II), and a mixture thereof, according to claim 1, the method comprising reacting compounds of formula (III) and of formula (IV), compounds of formula (III) being represented by:

(III)

compounds of formula (IV) being represented by:

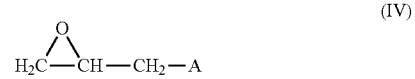
(IV)

wherein for preparation of compounds of formula (I), $R_{1b}$ and $R_{2b}$ are as defined in claim 1 for $R_1$ and $R_2$ respectively of formula (I), for preparation of compounds of formula (II), $R_{1b}$ and $R_{2b}$ are as defined in claim 1 for $R_{1a}$, and $R_{2a}$ respectively of formula (II), and A is a halogen.

3. A composition comprising at least one compound according to claim 1 and at least one further component.

4. The composition according to claim 3, wherein said further component is water.

5. A method for providing hydrophobicity comprising combining a cellulosic suspension with a compound chosen among compounds of formula (I), (II), (V), and mixtures thereof to provide hydrophobocity, wherein:

compounds of formula (I) are represented by:

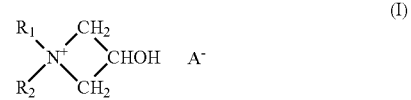
(I)

compounds of formula (II) are represented by:

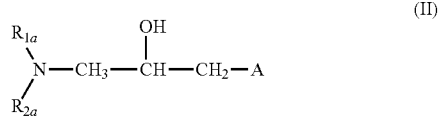
(II)

compounds of formula (V) are represented by:

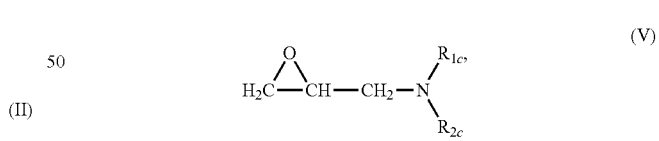
(V)

and wherein each of $R_1$, $R_2$, $R_{1a}$, $R_{2a}$, $R_{1c}$ and $R_{2c}$ is, independently from the others, a hydrocarbon having from 16 carbon atoms up to 30 carbon atoms, and A is a halogen.

6. The method according to claim 5, wherein each of $R_1$, $R_2$, $R_{1a}$, $R_{2a}$, $R_{1c}$ and $R_{2c}$ is, independently from the others, a hydrocarbon having from 16 carbon atoms up to 26 carbon atoms.

7. A process for manufacturing paper or paper board comprising providing an aqueous cellulosic suspension, dewatering the aqueous cellulosic suspension thereby providing a web of paper or paper board, the process comprising adding a compound chosen among compounds of formula (I), (II), (V), and mixtures thereof to the aqueous cellulosic suspension or to a web of paper or paper board, or both, wherein compounds of formula (I) are represented by:

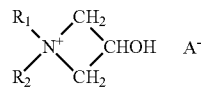
(I)

compounds of formula (II) are represented by:

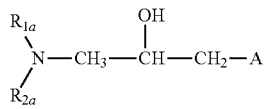
(II)

compounds of formula (V) are represented by:

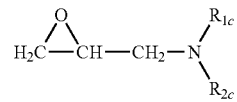
(V)

and wherein each of $R_1$, $R_2$, $R_{1a}$, $R_{2a}$, $R_{1c}$ and $R_{2c}$ is, independently of the others, a hydrocarbon having from 16 carbon atoms up to 30 carbon atoms, and A is a halogen.

8. The process for manufacturing paper or paper board according to claim 7, wherein the compound chosen among compounds of formula (I), formula (II), formula (V), and mixtures thereof is provided as an aqueous composition.

9. Paper or paper board obtainable by a process as defined in claim 7 wherein the paper or paper board comprises said compound chosen among compounds of formula (I), formula (II), formula (V), and mixtures thereof.

* * * * *